(12) United States Patent
Odorzynski et al.

(10) Patent No.: US 6,939,334 B2
(45) Date of Patent: Sep. 6, 2005

(54) THREE DIMENSIONAL PROFILING OF AN ELASTIC HOT MELT PRESSURE SENSITIVE ADHESIVE TO PROVIDE AREAS OF DIFFERENTIAL TENSION

(75) Inventors: Thomas W. Odorzynski, Green Bay, WI (US); Michael Joseph Garvey, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 579 days.

(21) Appl. No.: 10/025,026

(22) Filed: Dec. 19, 2001

(65) Prior Publication Data

US 2003/0114824 A1 Jun. 19, 2003

(51) Int. Cl.⁷ .................................................. A61F 13/15
(52) U.S. Cl. ............................ 604/385.24; 604/385.25; 428/343; 156/244.25
(58) Field of Search ........................ 156/244.11–244.27, 156/230

(56) References Cited

U.S. PATENT DOCUMENTS

| | | |
|---|---|---|
| 2,206,761 A | 7/1940 | Bergstein |
| 2,266,761 A | 12/1941 | Jackson, Jr., et al. |
| 2,357,392 A | 9/1944 | Francis, Jr. |
| 2,464,301 A | 3/1949 | Francis, Jr. |
| 2,483,405 A | 10/1949 | Francis, Jr. |
| 2,957,512 A | 10/1960 | Wade et al. |
| 2,957,852 A | 10/1960 | Frankenburg et al. |
| 3,186,893 A | 6/1965 | Mercer |
| 3,338,992 A | 8/1967 | Kinney |
| 3,341,394 A | 9/1967 | Kinney |
| 3,371,668 A | 3/1968 | Johnson |
| 3,391,048 A | 7/1968 | Dyer et al. |
| 3,439,085 A | 4/1969 | Hartmann |
| 3,449,187 A | 6/1969 | Bobkowicz |

(Continued)

FOREIGN PATENT DOCUMENTS

| | | |
|---|---|---|
| CA | 2165486 | 6/1996 |
| DE | 3423644 A1 | 1/1986 |
| DE | 3734963 A1 | 4/1988 |
| EP | 0155636 A2 | 9/1985 |

(Continued)

*Primary Examiner*—Jacqueline F. Stephens
(74) *Attorney, Agent, or Firm*—Pauley Petersen & Erickson

(57) ABSTRACT

Disclosed is a film formed from an elastomeric, hot melt, pressure-sensitive adhesive, with at least two different dimensions in the Z axis resulting in areas of differential tension when the film is stretched. The elastomeric and adhesive film further forms a liquid barrier. The elastomeric, hot melt, pressure-sensitive adhesive film with differential tension is particularly suitable for making a disposable absorbent garment.

39 Claims, 5 Drawing Sheets

U.S. PATENT DOCUMENTS

| | | | |
|---|---|---|---|
| 3,468,748 A | 9/1969 | Bassett | |
| 3,489,148 A | 1/1970 | Duncan et al. | |
| 3,502,538 A | 3/1970 | Petersen | |
| 3,502,763 A | 3/1970 | Hartmann | |
| 3,542,615 A | 11/1970 | Dobo et al. | |
| 3,575,782 A | 4/1971 | Hansen | |
| 3,616,129 A | 10/1971 | Sager | |
| 3,629,047 A | 12/1971 | Davison | |
| 3,669,823 A | 6/1972 | Wood | |
| 3,673,026 A | 6/1972 | Brown | |
| 3,676,242 A | 7/1972 | Prentice | |
| 3,689,342 A | 9/1972 | Vogt et al. | |
| 3,692,618 A | 9/1972 | Dorschner et al. | |
| 3,752,613 A | 8/1973 | Vogt et al. | |
| 3,773,590 A | 11/1973 | Morgan | |
| 3,802,817 A | 4/1974 | Matsuki et al. | |
| 3,806,289 A | 4/1974 | Schwarz | |
| 3,836,416 A | 9/1974 | Ropiequet | |
| 3,838,692 A | 10/1974 | Levesque | |
| 3,849,241 A | 11/1974 | Butin et al. | |
| 3,857,144 A | 12/1974 | Bustin | |
| 3,860,003 A | 1/1975 | Buell | |
| 3,890,184 A | 6/1975 | Morgan | |
| 3,904,465 A | 9/1975 | Haase et al. | |
| 3,912,567 A | 10/1975 | Schwartz | |
| 3,917,448 A | 11/1975 | Wood | |
| 3,932,328 A | 1/1976 | Korpman | |
| 3,949,128 A | 4/1976 | Ostermeier | |
| 3,949,130 A | 4/1976 | Sabee et al. | |
| 3,973,063 A | 8/1976 | Clayton | |
| 3,978,185 A | 8/1976 | Buntin et al. | |
| 3,979,050 A | 9/1976 | Cilia | |
| 4,013,816 A | 3/1977 | Sabee et al. | |
| 4,028,292 A | 6/1977 | Korpman | |
| 4,038,346 A | 7/1977 | Feeney | |
| 4,080,348 A | 3/1978 | Korpman | |
| 4,090,385 A | 5/1978 | Packard | |
| 4,107,364 A | 8/1978 | Sisson | |
| 4,148,676 A | 4/1979 | Paquette et al. | |
| 4,209,563 A | 6/1980 | Sisson | |
| 4,211,807 A | 7/1980 | Yazawa et al. | |
| 4,239,578 A | 12/1980 | Gore | |
| 4,241,123 A | 12/1980 | Shih | |
| 4,248,652 A | 2/1981 | Civardi et al. | |
| 4,259,220 A | 3/1981 | Bunnelle et al. | |
| 4,285,998 A | 8/1981 | Thibodeau | |
| 4,300,562 A | 11/1981 | Pieniak | |
| 4,302,495 A | 11/1981 | Marra | |
| 4,303,571 A | 12/1981 | Jansen et al. | |
| 4,304,234 A | 12/1981 | Hartmann | |
| 4,310,594 A | 1/1982 | Yamazaki et al. | |
| 4,319,572 A | 3/1982 | Widlund et al. | |
| 4,323,534 A | 4/1982 | DesMarais | |
| 4,333,782 A | 6/1982 | Pieniak | |
| 4,340,558 A | 7/1982 | Hendrickson | |
| 4,340,563 A | 7/1982 | Appel et al. | |
| 4,375,446 A | 3/1983 | Fujii et al. | |
| 4,402,688 A | 9/1983 | Julemont | |
| 4,405,397 A | 9/1983 | Teed | |
| 4,413,623 A | 11/1983 | Pieniak | |
| 4,417,935 A | 11/1983 | Spencer | |
| 4,418,123 A | 11/1983 | Bunnelle et al. | |
| 4,438,167 A | 3/1984 | Schwarz | |
| 4,440,819 A | 4/1984 | Rosser et al. | |
| 4,490,427 A | 12/1984 | Grant et al. | |
| 4,496,417 A | 1/1985 | Haake et al. | |
| 4,500,316 A | 2/1985 | Damico | |
| 4,507,163 A | 3/1985 | Menard | |
| 4,522,863 A | 6/1985 | Keck et al. | |
| 4,525,407 A | 6/1985 | Ness | |
| 4,543,099 A | 9/1985 | Bunnelle et al. | |
| 4,548,859 A | 10/1985 | Kline et al. | |
| 4,552,795 A | 11/1985 | Hansen et al. | |
| 4,555,811 A | 12/1985 | Shimalla | |
| 4,572,752 A | 2/1986 | Jensen et al. | |
| 4,586,199 A | 5/1986 | Birring | |
| D284,036 S | 6/1986 | Birring | |
| 4,606,964 A | 8/1986 | Wideman | |
| 4,618,384 A | 10/1986 | Sabee | |
| 4,626,305 A | 12/1986 | Suzuki et al. | |
| 4,636,419 A | 1/1987 | Madsen et al. | |
| 4,640,859 A | 2/1987 | Hansen et al. | |
| 4,644,045 A | 2/1987 | Fowells | |
| 4,652,487 A | 3/1987 | Morman | |
| 4,656,081 A | 4/1987 | Ando et al. | |
| 4,657,793 A | 4/1987 | Fisher | |
| 4,657,802 A | 4/1987 | Morman | |
| 4,661,389 A | 4/1987 | Mudge et al. | |
| 4,663,220 A | 5/1987 | Wisneski et al. | |
| 4,666,543 A | 5/1987 | Kawano | |
| 4,675,068 A | 6/1987 | Lundmark | |
| 4,683,877 A | 8/1987 | Ersfeld et al. | |
| 4,687,477 A | 8/1987 | Suzuki et al. | |
| 4,692,368 A | 9/1987 | Taylor et al. | |
| 4,692,371 A | 9/1987 | Morman et al. | |
| 4,704,116 A | 11/1987 | Enloe | |
| 4,718,901 A | 1/1988 | Singheimer | |
| 4,719,261 A | 1/1988 | Bunnelle et al. | |
| 4,720,415 A | 1/1988 | Vander Wielen et al. | |
| 4,725,468 A | 2/1988 | McIntyre | |
| 4,726,874 A | 2/1988 | VanVliet | |
| 4,734,311 A | 3/1988 | Sokolowski | |
| 4,734,320 A | 3/1988 | Ohira et al. | |
| 4,734,447 A | 3/1988 | Hattori et al. | |
| 4,735,673 A | 4/1988 | Piron | |
| 4,756,942 A | 7/1988 | Aichele | |
| 4,761,198 A | 8/1988 | Salerno | |
| 4,762,582 A | 8/1988 | de Jonckheere | |
| 4,775,579 A | 10/1988 | Hagy et al. | |
| 4,777,080 A | 10/1988 | Harris, Jr. et al. | |
| 4,789,699 A | 12/1988 | Kieffer et al. | |
| 4,798,603 A | 1/1989 | Meyer et al. | |
| 4,801,345 A | 1/1989 | Dussaud et al. | |
| 4,801,482 A | 1/1989 | Goggans et al. | |
| 4,803,117 A | 2/1989 | Daponte | |
| 4,804,577 A | 2/1989 | Hazelton et al. | |
| 4,816,094 A | 3/1989 | Pomplun et al. | |
| 4,818,597 A | 4/1989 | DaPonte et al. | |
| 4,826,415 A | 5/1989 | Mende | |
| 4,837,715 A | 6/1989 | Ungpiyakul et al. | |
| 4,842,666 A | 6/1989 | Werenicz | |
| 4,854,985 A | 8/1989 | Soderlund et al. | |
| 4,854,989 A | 8/1989 | Singheimer | |
| 4,863,779 A | 9/1989 | Daponte | |
| 4,867,735 A | 9/1989 | Wogelius | |
| 4,874,447 A | 10/1989 | Hazelton et al. | |
| 4,883,482 A | 11/1989 | Gandrez et al. | |
| 4,883,549 A | 11/1989 | Frost et al. | |
| 4,891,258 A | 1/1990 | Fahrenkrug | |
| 4,892,536 A | 1/1990 | DesMarais et al. | |
| 4,892,903 A | 1/1990 | Himes | |
| 4,900,619 A | 2/1990 | Ostrowski et al. | |
| 4,906,507 A | 3/1990 | Grynaeus et al. | |
| 4,908,247 A | 3/1990 | Baird et al. | |
| 4,908,253 A | 3/1990 | Rasmussen | |
| 4,910,064 A | 3/1990 | Sabee | |
| 4,917,696 A | 4/1990 | De Jonckheere | |
| 4,917,746 A | 4/1990 | Kons et al. | |
| 4,929,492 A | 5/1990 | Carey, Jr. et al. | |
| 4,935,021 A | 6/1990 | Huffman et al. | |
| 4,938,757 A | 7/1990 | Van Gompel et al. | |

| 4,938,821 A | 7/1990 | Soderlund et al. | 5,364,382 A | 11/1994 | Latimer et al. |
|---|---|---|---|---|---|
| 4,940,464 A | 7/1990 | Van Gompel et al. | 5,366,793 A | 11/1994 | Fitts, Jr. et al. |
| 4,965,122 A | 10/1990 | Morman | 5,376,198 A | 12/1994 | Fahrenkrug et al. |
| 4,968,313 A | 11/1990 | Sabee | 5,376,430 A | 12/1994 | Swenson et al. |
| 4,970,259 A | 11/1990 | Mitchell et al. | 5,382,400 A | 1/1995 | Pike et al. |
| 4,977,011 A | 12/1990 | Smith | 5,385,775 A | 1/1995 | Wright |
| 4,984,584 A | 1/1991 | Hansen et al. | 5,389,173 A | 2/1995 | Merkatoris et al. |
| 4,994,508 A | 2/1991 | Shiraki et al. | 5,393,599 A | 2/1995 | Quantrille et al. |
| 4,995,928 A | 2/1991 | Sabee | 5,399,219 A | 3/1995 | Roessler et al. |
| 4,998,929 A | 3/1991 | Bjorksund et al. | 5,405,682 A | 4/1995 | Shawyer et al. |
| 5,000,806 A | 3/1991 | Merkatoris et al. | 5,407,507 A | 4/1995 | Ball |
| 5,002,815 A | 3/1991 | Yamanaka et al. | 5,411,618 A | 5/1995 | Jocewicz, Jr. |
| 5,005,215 A | 4/1991 | McIlquham | 5,413,654 A | 5/1995 | Igaue et al. |
| 5,013,785 A | 5/1991 | Mizui | 5,413,849 A | 5/1995 | Austin et al. |
| 5,028,646 A | 7/1991 | Miller et al. | 5,415,644 A | 5/1995 | Enloe |
| 5,034,008 A | 7/1991 | Breitkopf | 5,415,649 A | 5/1995 | Watanabe et al. |
| 5,045,133 A | 9/1991 | DaPonte et al. | 5,415,925 A | 5/1995 | Austin et al. |
| 5,046,272 A | 9/1991 | Vogt et al. | 5,422,172 A | 6/1995 | Wu |
| 5,060,349 A | 10/1991 | Walton et al. | 5,425,987 A | 6/1995 | Shawver et al. |
| 5,073,436 A | 12/1991 | Antonacci et al. | 5,429,629 A | 7/1995 | Latimer et al. |
| 5,093,422 A | 3/1992 | Himes | 5,429,694 A | 7/1995 | Herrmann |
| 5,100,435 A | 3/1992 | Onwumere | 5,431,644 A | 7/1995 | Sipinen et al. |
| 5,104,116 A | 4/1992 | Pohjola | 5,431,991 A | 7/1995 | Quantrille et al. |
| 5,108,820 A | 4/1992 | Kaneko et al. | 5,447,462 A | 9/1995 | Smith et al. |
| 5,112,889 A | 5/1992 | Miller et al. | 5,447,508 A | 9/1995 | Numano et al. |
| 5,114,087 A | 5/1992 | Fisher et al. | 5,449,353 A | 9/1995 | Watanabe et al. |
| 5,116,662 A | 5/1992 | Morman | 5,464,401 A | 11/1995 | Hasse et al. |
| 5,147,487 A | 9/1992 | Nomura et al. | 5,472,775 A | 12/1995 | Obijeski et al. |
| 5,163,932 A | 11/1992 | Nomura et al. | 5,476,458 A | 12/1995 | Glaug et al. |
| D331,627 S | 12/1992 | Igaue et al. | 5,476,563 A | 12/1995 | Nakata |
| 5,169,706 A | 12/1992 | Collier, IV et al. | 5,484,645 A | 1/1996 | Lickfield et al. |
| 5,169,712 A | 12/1992 | Tapp | 5,486,166 A | 1/1996 | Bishop et al. |
| 5,176,668 A | 1/1993 | Bernardin | 5,490,846 A | 2/1996 | Ellis et al. |
| 5,176,672 A | 1/1993 | Bruemmer et al. | 5,496,298 A | 3/1996 | Kuepper et al. |
| 5,186,779 A | 2/1993 | Tubbs | 5,498,468 A | 3/1996 | Blaney |
| 5,192,606 A | 3/1993 | Proxmire et al. | 5,500,075 A | 3/1996 | Herrmann |
| 5,198,281 A | 3/1993 | Muzzy et al. | 5,501,679 A | 3/1996 | Krueger et al. |
| 5,200,246 A | 4/1993 | Sabee | 5,509,915 A | 4/1996 | Hanson et al. |
| 5,204,429 A | 4/1993 | Kaminsky et al. | 5,514,470 A | 5/1996 | Haffner et al. |
| D335,707 S | 5/1993 | Igaue et al. | 5,516,476 A | 5/1996 | Haggard et al. |
| 5,209,801 A | 5/1993 | Smith | 5,523,146 A | 6/1996 | Bodford et al. |
| 5,219,633 A | 6/1993 | Sabee | 5,527,300 A | 6/1996 | Sauer |
| 5,224,405 A | 7/1993 | Pohjola | 5,531,850 A | 7/1996 | Herrmann |
| 5,226,992 A | 7/1993 | Morman | 5,534,330 A | 7/1996 | Groshens |
| 5,229,191 A | 7/1993 | Austin | 5,540,796 A | 7/1996 | Fries |
| 5,232,777 A | 8/1993 | Sipinen et al. | 5,540,976 A | 7/1996 | Shawver et al. |
| 5,236,430 A | 8/1993 | Bridges | 5,543,206 A | 8/1996 | Austin et al. |
| 5,236,770 A | 8/1993 | Assent et al. | 5,545,158 A | 8/1996 | Jessup |
| 5,238,733 A | 8/1993 | Joseph et al. | 5,545,285 A | 8/1996 | Johnson |
| 5,246,433 A | 9/1993 | Hasse et al. | 5,549,964 A | 8/1996 | Shohji et al. |
| D340,283 S | 10/1993 | Igaue et al. | 5,569,232 A | 10/1996 | Roe et al. |
| 5,252,170 A | 10/1993 | Schaupp | 5,575,783 A | 11/1996 | Clear et al. |
| 5,259,902 A | 11/1993 | Muckenfuhs | 5,576,090 A | 11/1996 | Suzuki |
| 5,260,126 A | 11/1993 | Collier, IV et al. | 5,582,668 A | 12/1996 | Kling |
| 5,272,236 A | 12/1993 | Lai et al. | 5,591,152 A | 1/1997 | Buell et al. |
| 5,278,272 A | 1/1994 | Lai et al. | 5,591,792 A | 1/1997 | Hattori et al. |
| 5,288,791 A | 2/1994 | Collier, IV et al. | 5,595,618 A | 1/1997 | Fries et al. |
| 5,290,842 A | 3/1994 | Sasaki et al. | 5,597,430 A | 1/1997 | Rasche |
| 5,296,080 A | 3/1994 | Merkatoris et al. | 5,612,118 A | 3/1997 | Schleinz et al. |
| 5,304,599 A | 4/1994 | Himes | 5,614,276 A | 3/1997 | Petsetakis |
| 5,308,345 A | 5/1994 | Herrin | 5,620,780 A | 4/1997 | Krueger et al. |
| 5,312,500 A | 5/1994 | Kurihara et al. | 5,624,740 A | 4/1997 | Nakata |
| 5,324,580 A | 6/1994 | Allan et al. | 5,626,573 A | 5/1997 | Igaue et al. |
| 5,332,613 A | 7/1994 | Taylor et al. | 5,628,856 A | 5/1997 | Dobrin et al. |
| 5,334,437 A | 8/1994 | Zafiroglu | 5,645,672 A | 7/1997 | Dobrin |
| 5,334,446 A | 8/1994 | Quantrille et al. | 5,652,041 A | 7/1997 | Buerger et al. |
| 5,336,545 A | 8/1994 | Morman | 5,660,664 A | 8/1997 | Herrmann |
| 5,336,552 A | 8/1994 | Strack et al. | 5,663,228 A | 9/1997 | Sasaki et al. |
| 5,342,341 A | 8/1994 | Igaue et al. | 5,669,897 A | 9/1997 | Lavon et al. |
| 5,342,469 A | 8/1994 | Bodford et al. | 5,674,216 A | 10/1997 | Buell et al. |
| 5,360,854 A | 11/1994 | Bozich, Jr. | 5,680,653 A | 10/1997 | Mathis et al. |

| | | |
|---|---|---|
| 5,681,302 A | 10/1997 | Melbye et al. |
| 5,683,787 A | 11/1997 | Boich et al. |
| 5,690,626 A | 11/1997 | Suzuki et al. |
| 5,691,034 A | 11/1997 | Krueger et al. |
| 5,693,038 A | 12/1997 | Suzuki et al. |
| 5,695,849 A | 12/1997 | Shawver et al. |
| 5,702,378 A | 12/1997 | Widlund et al. |
| 5,707,709 A | 1/1998 | Blake |
| 5,709,921 A | 1/1998 | Shawver |
| 5,720,838 A | 2/1998 | Nakata |
| 5,733,635 A | 3/1998 | Terakawa et al. |
| 5,733,822 A | 3/1998 | Gessner et al. |
| 5,735,839 A | 4/1998 | Kawaguchi et al. |
| 5,736,219 A | 4/1998 | Suehr et al. |
| 5,746,731 A | 5/1998 | Hisada |
| 5,749,865 A | 5/1998 | Yamamoto et al. |
| 5,749,866 A | 5/1998 | Roe et al. |
| 5,766,389 A | 6/1998 | Brandon et al. |
| 5,766,737 A | 6/1998 | Willey et al. |
| 5,769,838 A | 6/1998 | Buell et al. |
| 5,769,993 A | 6/1998 | Baldauf |
| 5,772,649 A | 6/1998 | Siudzinski |
| 5,773,373 A | 6/1998 | Wynne et al. |
| 5,773,374 A | 6/1998 | Wood et al. |
| 5,788,804 A | 8/1998 | Horsting |
| 5,789,065 A | 8/1998 | Haffner et al. |
| 5,789,328 A | 8/1998 | Kurihara et al. |
| 5,789,474 A | 8/1998 | Lu et al. |
| 5,800,903 A | 9/1998 | Wood et al. |
| 5,804,021 A | 9/1998 | Abuto et al. |
| 5,804,286 A | 9/1998 | Quantrille et al. |
| 5,814,176 A | 9/1998 | Proulx |
| 5,817,087 A | 10/1998 | Takabayashi et al. |
| 5,818,719 A | 10/1998 | Brandon et al. |
| 5,830,203 A | 11/1998 | Suzuki et al. |
| 5,834,089 A | 11/1998 | Jones et al. |
| 5,836,931 A | 11/1998 | Toyoda et al. |
| 5,836,932 A | 11/1998 | Buell et al. |
| 5,840,412 A | 11/1998 | Wood et al. |
| 5,840,633 A | 11/1998 | Kurihara et al. |
| 5,846,232 A | 12/1998 | Serbiak et al. |
| 5,849,001 A | 12/1998 | Torimae et al. |
| 5,856,387 A | 1/1999 | Sasaki et al. |
| 5,860,945 A | 1/1999 | Cramer et al. |
| 5,865,933 A | 2/1999 | Morin et al. |
| 5,876,392 A | 3/1999 | Hisada |
| 5,879,776 A | 3/1999 | Nakata |
| 5,882,573 A | 3/1999 | Kwok et al. |
| 5,885,656 A | 3/1999 | Goldwasser |
| 5,885,686 A | 3/1999 | Cederblad et al. |
| 5,895,382 A | 4/1999 | Popp et al. |
| 5,897,546 A | 4/1999 | Kido et al. |
| 5,899,895 A | 5/1999 | Robles et al. |
| 5,902,540 A | 5/1999 | Kwok |
| 5,904,298 A | 5/1999 | Kwok et al. |
| 5,916,206 A | 6/1999 | Otsubo et al. |
| 5,921,973 A | 7/1999 | Newkirk et al. |
| 5,930,139 A | 7/1999 | Chapdelaine et al. |
| 5,931,581 A | 8/1999 | Garberg et al. |
| 5,932,039 A | 8/1999 | Popp et al. |
| 5,941,865 A | 8/1999 | Otsubo et al. |
| D414,262 S | 9/1999 | Ashton et al. |
| 5,952,252 A | 9/1999 | Shawver et al. |
| 5,964,970 A | 10/1999 | Woolwine et al. |
| 5,964,973 A | 10/1999 | Heath et al. |
| 5,990,377 A | 11/1999 | Chen et al. |
| 5,993,433 A | 11/1999 | St. Louis et al. |
| 5,997,521 A | 12/1999 | Robles et al. |
| 6,004,306 A | 12/1999 | Robles et al. |
| 6,009,558 A | 1/2000 | Rosch et al. |
| 6,033,502 A | 3/2000 | Coenen et al. |
| 6,045,543 A | 4/2000 | Pozniak et al. |
| 6,048,326 A | 4/2000 | Davis et al. |
| 6,057,024 A | 5/2000 | Mleziva et al. |
| 6,066,369 A | 5/2000 | Schulz et al. |
| 6,087,550 A | 7/2000 | Anderson-Fischer et al. |
| 6,090,234 A | 7/2000 | Barone et al. |
| 6,092,002 A | 7/2000 | Kastman et al. |
| 6,093,663 A | 7/2000 | Ouellette et al. |
| 6,096,668 A | 8/2000 | Abuto et al. |
| 6,123,694 A | 9/2000 | Pieniak et al. |
| 6,132,410 A | 10/2000 | Van Gompel et al. |
| 6,152,904 A | 11/2000 | Matthews et al. |
| 6,169,848 B1 | 1/2001 | Henry |
| 6,183,587 B1 | 2/2001 | McFall et al. |
| 6,183,847 B1 | 2/2001 | Goldwasser |
| 6,197,012 B1 | 3/2001 | Mishima et al. |
| 6,214,476 B1 | 4/2001 | Ikeda et al. |
| 6,217,690 B1 | 4/2001 | Rajala et al. |
| 6,221,483 B1 | 4/2001 | Hilston et al. |
| 6,231,557 B1 | 5/2001 | Krautkramer et al. |
| 6,238,379 B1 | 5/2001 | Keuhn, Jr. et al. |
| 6,245,050 B1 | 6/2001 | Odorzynski et al. |
| 6,245,168 B1 | 6/2001 | Coenen et al. |
| 6,260,211 B1 | 7/2001 | Rajala et al. |
| 6,279,807 B1 | 8/2001 | Crowley et al. |
| 6,290,979 B1 | 9/2001 | Roe et al. |
| 6,310,164 B1 | 10/2001 | Morizono et al. |
| 6,316,013 B1 | 11/2001 | Paul et al. |
| 6,316,687 B1 | 11/2001 | Davis et al. |
| 6,316,688 B1 | 11/2001 | Hammons et al. |
| 6,320,096 B1 | 11/2001 | Inoue et al. |
| 6,323,389 B1 | 11/2001 | Thomas et al. |
| 6,329,459 B1 | 12/2001 | Kang et al. |
| 6,364,863 B1 | 4/2002 | Yamamoto et al. |
| 6,365,659 B1 | 4/2002 | Aoyama et al. |
| 6,475,600 B1 | 11/2002 | Morman et al. |
| 6,537,935 B1 | 3/2003 | Seth et al. |
| 6,562,167 B2 | 5/2003 | Coenen et al. |
| 2002/0002021 A1 | 1/2002 | May et al. |
| 2002/0009940 A1 | 1/2002 | May et al. |
| 2002/0019616 A1 | 2/2002 | Thomas |
| 2002/0104608 A1 | 8/2002 | Welch et al. |
| 2002/0138063 A1 | 9/2002 | Kuen et al. |
| 2002/0164465 A1 | 11/2002 | Curro et al. |

FOREIGN PATENT DOCUMENTS

| | | |
|---|---|---|
| EP | 0239080 A2 | 9/1987 |
| EP | 0172037 B1 | 2/1989 |
| EP | 0380781 A2 | 8/1990 |
| EP | 0396800 B1 | 11/1990 |
| EP | 0456885 B1 | 11/1991 |
| EP | 0217032 B1 | 2/1992 |
| EP | 06891815 A1 | 1/1996 |
| EP | 0713546 B1 | 3/1997 |
| EP | 0570980 B1 | 7/1997 |
| EP | 0814189 A1 | 12/1997 |
| EP | 0582569 B1 | 6/1998 |
| EP | 0873738 A2 | 10/1998 |
| EP | 0604731 B1 | 6/1999 |
| EP | 1013251 A1 | 6/2000 |
| EP | 0547497 B2 | 7/2000 |
| EP | 0743052 B1 | 11/2000 |
| EP | 0888101 B1 | 5/2001 |
| EP | 0761193 B1 | 12/2001 |
| EP | 0761194 B1 | 12/2001 |
| EP | 0763353 B1 | 6/2002 |
| EP | 0787474 B1 | 7/2002 |
| EP | 0617939 B1 | 8/2002 |
| EP | 0688550 B2 | 8/2002 |
| EP | 0806196 B1 | 8/2002 |
| EP | 0901780 B1 | 1/2003 |

| | | | | | | |
|---|---|---|---|---|---|---|
| EP | 0753292 B1 | 4/2003 | | WO | WO 96/35402 | 11/1996 |
| GB | 2244422 A | 12/1991 | | WO | WO 97/17046 | 5/1997 |
| GB | 2267024 A | 11/1993 | | WO | WO 98/14156 | 4/1998 |
| GB | 2253131 B | 10/1994 | | WO | WO 98/49988 | 11/1998 |
| GB | 2250921 B | 6/1995 | | WO | WO 98/55062 | 12/1998 |
| GB | 2268389 B | 7/1996 | | WO | WO 99/17926 | 4/1999 |
| IL | 92891 | 2/1992 | | WO | WO 99/24519 | 5/1999 |
| JP | 3-67646 | 3/1991 | | WO | WO 99/47590 | 9/1999 |
| JP | 10-075978 A2 | 3/1998 | | WO | WO 99/60969 | 12/1999 |
| JP | 10-165438 | 6/1998 | | WO | WO 99/60970 | 12/1999 |
| WO | WO 90/03464 | 4/1990 | | WO | WO 99/60971 | 12/1999 |
| WO | WO 91/07277 | 5/1991 | | WO | WO 00/10500 | 3/2000 |
| WO | WO 92/16371 | 10/1992 | | WO | WO 00/29199 | 5/2000 |
| WO | WO 93/15247 | 8/1993 | | WO | WO 00/37003 | 6/2000 |
| WO | WO 93/17648 | 9/1993 | | WO | WO 00/37005 | 6/2000 |
| WO | WO 94/09736 | 5/1994 | | WO | WO 00/37723 | 6/2000 |
| WO | WO 95/03443 | 2/1995 | | WO | WO 00/59429 | 10/2000 |
| WO | WO 95/04182 | 2/1995 | | WO | WO 01/00053 A1 | 1/2001 |
| WO | WO 95/16425 | 6/1995 | | WO | WO 01/32116 A1 | 5/2001 |
| WO | WO 95/16562 | 6/1995 | | WO | WO 01/49907 A2 | 7/2001 |
| WO | WO 95/34264 | 12/1995 | | WO | WO 01/87214 A1 | 11/2001 |
| WO | WO 96/13989 | 5/1996 | | WO | WO 02/34184 A1 | 5/2002 |
| WO | WO 96/23466 | 8/1996 | | WO | WO 02/060690 A2 | 8/2002 |

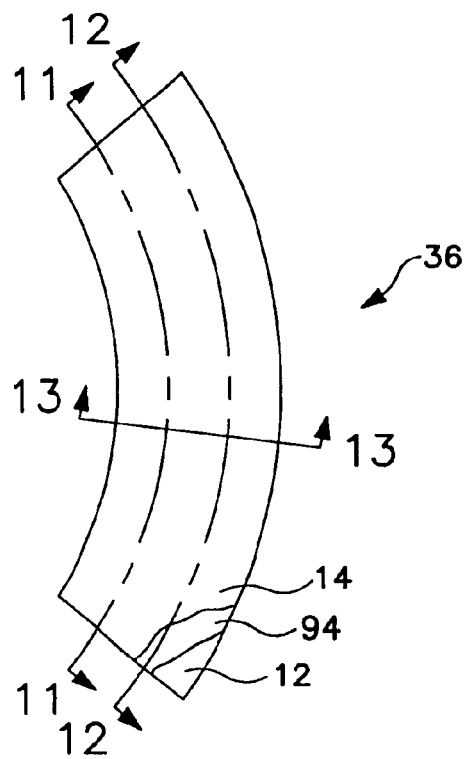
FIG. 10
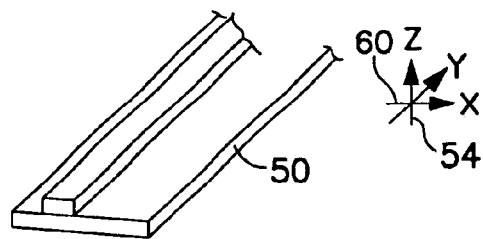
FIG. 14
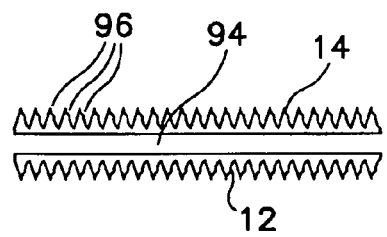
FIG. 11
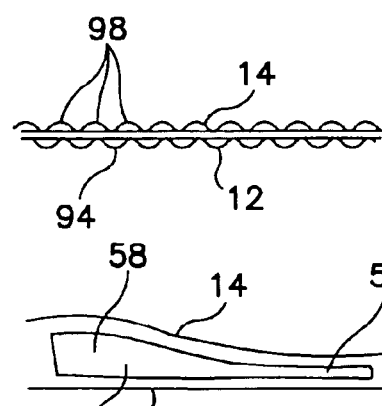
FIG. 12
FIG. 13

THREE DIMENSIONAL PROFILING OF AN ELASTIC HOT MELT PRESSURE SENSITIVE ADHESIVE TO PROVIDE AREAS OF DIFFERENTIAL TENSION

BACKGROUND OF THE INVENTION

The use of elastomeric materials to form elasticized areas in the design and construction of disposable absorbent articles is well known. Typically, such elasticized areas are formed by bonding elastomeric materials, such as natural or synthetic rubber, to the other components from which such disposable absorbent articles are formed. Generally, the elastomeric materials will be bonded to the absorbent article while the elastomeric materials are in a stretched condition. Upon relaxation, the elastomeric materials will operate to gather the components of the disposable absorbent articles to which they are attached. In this manner, elastomeric leg cuffs and waist gathers can be formed.

Attaching elastomeric materials to a disposable absorbent article while said elastomeric materials are in a stretched condition may be, from a manufacturing perspective, a difficult step to accomplish. Moreover, such elastomeric materials are typically attached to the disposable absorbent article through the use of adhesives such as hot melt adhesives. However, the presence of such adhesive has been found to reduce or eliminate the retractive forces exerted by such elastomeric material in the area in which the adhesives contact the elastomeric material and the disposable absorbent article to which they are attached.

The need for increased fit and comfort of disposable absorbent garments has resulted in the development of elastomeric films having differential elasticity, or so called targeted elastic zones. Films or materials constructed to have targeted elastic zones, or areas of differential tension when stretched, are disclosed in copending U.S. application Ser. No. 09/855,194, filed 14 May 2001, and of common ownership herewith. The incorporation of the differential elasticity of targeted elastics into films has furthered the ease of manufacture and resulted in improved comfort, functionality, and appearance. Other elastomeric films have been developed which are desirable in several aspects for the manufacture of absorbent garments. As disclosed in U.S. Pat. No. 6,245,050, issued 12 Jun. 2001 to Odorzynski et al., of common ownership herewith, an elastomeric film for use in disposable absorbent articles is taught which is a pressure sensitive adhesive and which provides liquid barrier properties with some vapor transmission. These films are hot melt extruded pressure-sensitive adhesives sometimes referred to as EBA (Elastic Barrier Adhesive).

In order to further improve the economy of manufacture and processability of the garments and the overall fit and comfort of such garments, it would be desirable to have a targeted elastic material that is easily manufactured as a targeted elastic film, is adhesive to other garment components with minimal processing steps, and which provides a liquid barrier suitable for use in the critical leakage areas of garment openings such as the leg holes or waist area of an undergarment pant structure.

SUMMARY OF THE INVENTION

The elastomeric material of the present invention is, at a first level, a pressure sensitive adhesive elastomeric film with differential elasticity owing to a differential thickness of material in its "Z" direction, i.e. perpendicular to the major X-Y plane of the film, with the film further being a liquid barrier. According to one embodiment the film will also exhibit some vapor transmission. The targeted elastic zone of the film may further be enhanced by providing different compositions of elastomer within discrete areas of the film.

The present invention is directed in some embodiments to an elastic laminate using such film, especially as used for a garment having one or more garment openings for the wearer's waist, legs, arms, and the like. The elastic laminate may combine the film with additional material such as facing sheets, to make a single composite material, sometimes referred to as a targeted elastic material ("TEM") having a targeted elastic zone of relatively higher tension, which may be aligned with the garment opening or openings for increased comfort and better fit and functionality of the garment.

The film, or a laminate using the film, may have a substantially homogeneous appearance, and does not have separately manufactured elastic components fused together. Rather the film is manufactured from a hot melt extrusion process as an integral unit. The present invention possesses inherent advantages of the hot melt manufacturing process.

A film according to the present invention will have different elastic properties at different regions, and exhibit greater elastic tension or greater elongation, or both, in a selected region of the film. In one embodiment this may come from a single composition which is hot melt extruded through a shaped die to impart different Z axis dimensions across the X-Y plane of the film. In another embodiment the different Z axis dimensions may result from coextrusion of two different compositions with similar overall properties but having different elasticity to impart further differential elasticity to the film.

The film of the present invention provides good adhesion to surrounding fabric, provides processing advantages such as ease of manufacture and handling, and provides good post-processing appearance. Furthermore, the film can be produced according to the present invention without the use of a separately manufactured or attached elastic band, and provides easier and less expensive manufacture of garments than those having previously known elastic systems.

With the foregoing in mind, it is a feature and advantage of the invention to provide an easily manufactured and handled elastomeric film material having regions of differential elasticity, which can serve as a pressure-sensitive adhesive and a liquid barrier, and the use of such a film with a garment having at least one elastic region.

The present invention will be described in detail with respect to an elasticized containment gasket utilized in a disposable absorbent garment such as a diaper, although the person having ordinary skill in the art will recognize that the present invention will have numerous applications in the field of fabrics, garment construction, and disposable absorbent articles manufacture, including but not limited to, incontinence products, catamenial products, medical wraps and garments. Because the present invention gives the garment designer freedom to accurately place elastomerics with preselected areas of differential tension, the overall fit and functionality of a garment can be more closely tailored to a variety of garment designs.

The present invention may be used to create gasketing around neck openings, arm openings, wrist openings, waist openings, leg openings, ankle openings, and any other opening surrounding a body part wherein fluid transfer resistance is desirable.

In another aspect, the present invention is directed to a disposable absorbent article having a length and a width and defining first and second waist portions and first and second longitudinal marginal portions. The absorbent article comprises the following components: a backsheet layer, a topsheet layer, and an absorbent structure located between said topsheet layer and said backsheet layer. The disposable absorbent article further includes at least one elasticized area formed from an elastomeric, hot melt, pressure-sensitive adhesive film having areas of differential elasticity, and a first component and a second component, said first and second components being adhered to one another by said elastomeric, hot melt, pressure-sensitive adhesive film. The elastomeric, hot melt, pressure-sensitive adhesive film having differential tension and the elasticized area formed therewith may have one or more of the following properties:

A. an adhesive bond strength sufficient to adhere the first and second components together during use of said disposable absorbent article;

B. an elongation in one area of the elastomer of at least 50 percent;

C. a retractive force in one area of the elastomer of less than 400 grams force per 2.54 cm (1.0 inch) width at 90 percent elongation;

D. a viscosity of less than 70,000 centipoise at 177 degrees C.; and

E. a cold flow value in one area of the elastomer of less than 20 percent at 54 degrees C.

DEFINITIONS

The terms "elastic" and "elastomeric" are used interchangeably to mean a material that is generally capable of recovering its shape after deformation when the deforming force is removed.

The term "gasket" or "gasket region" refers to a region of a garment which exhibits a moderate level of elastic tension against a wearer's body during use, and which restricts the flow of liquid and other material through a garment opening between the inside and outside of the garment. The term "fluid sealing gasket" is synonymous with these terms.

The term "targeted elastic regions" refers to isolated, often relatively narrow regions or zones in a single material or composite layer, which have greater elastic tension and/or elongation than adjacent or surrounding regions.

The term "elastic tension" refers to the amount of force per unit width required to stretch an elastic material (or a selected zone thereof) to a given percent elongation.

The term "elongation" refers to the capability of an elastic material to be stretched a certain distance, such that greater elongation refers to an elastic material capable of being stretched a greater distance than an elastic material having lower elongation.

The term "low tension zone" or "lower tension zone" refers to a zone or region in a material having one or more areas with low elastic tension characteristics relative to a high tension zone, when a stretching or biasing force is applied to the material. Thus, when a biasing force is applied to the material, the low tension zone will stretch more easily than the high tension zone. At 50% elongation of the fabric, the high tension zone may exhibit elastic tension at least 10% greater than the low tension zone. The terms "high tension zone" and "low tension zone" are relative, and the material may have multiple zones of different tensions.

The term "nonwoven fabric or web" means a web having a structure of individual fibers or filaments which are interlaid, but not in an identifiable manner as in a knitted fabric.

As used herein, the term "spunbond fibers" refers to small diameter fibers which are formed by extruding molten thermoplastic material as filaments from a plurality of fine, usually circular capillaries of a spinneret as taught, for example, by U.S. Pat. No. 4,340,563 to Appel et al. and U.S. Pat. No. 3,802,817 to Matsuki et al.

BRIEF DESCRIPTION OF THE DRAWINGS

FIG. 10 illustrates, a top, view of a differentially tensioned section of EBA film having nonwoven facing layers.

FIGS. 11–13 illustrate cross sectional views taken along lines 11—11, 12—12 and 13—13 of FIG. 10.

FIG. 14 illustrates a shape of an EBA film with a variable Z axis dimension as produced for Example 4 herein.

DETAILED DESCRIPTION OF THE PREFERRED EMBODIMENTS

A film according to the present invention is used efficaciously with a disposable absorbent article. The term "disposable absorbent article" refers to disposable articles intended to absorb body fluids. Examples of disposable absorbent articles include diapers, adult incontinence products, training pants, feminine napkins, wound dressings, and the like. For ease of understanding, much of the following description will be made in terms of a disposable diaper. Nonetheless, it is to be understood that the present invention may be suited for use on any disposable absorbent article.

Figure 1:
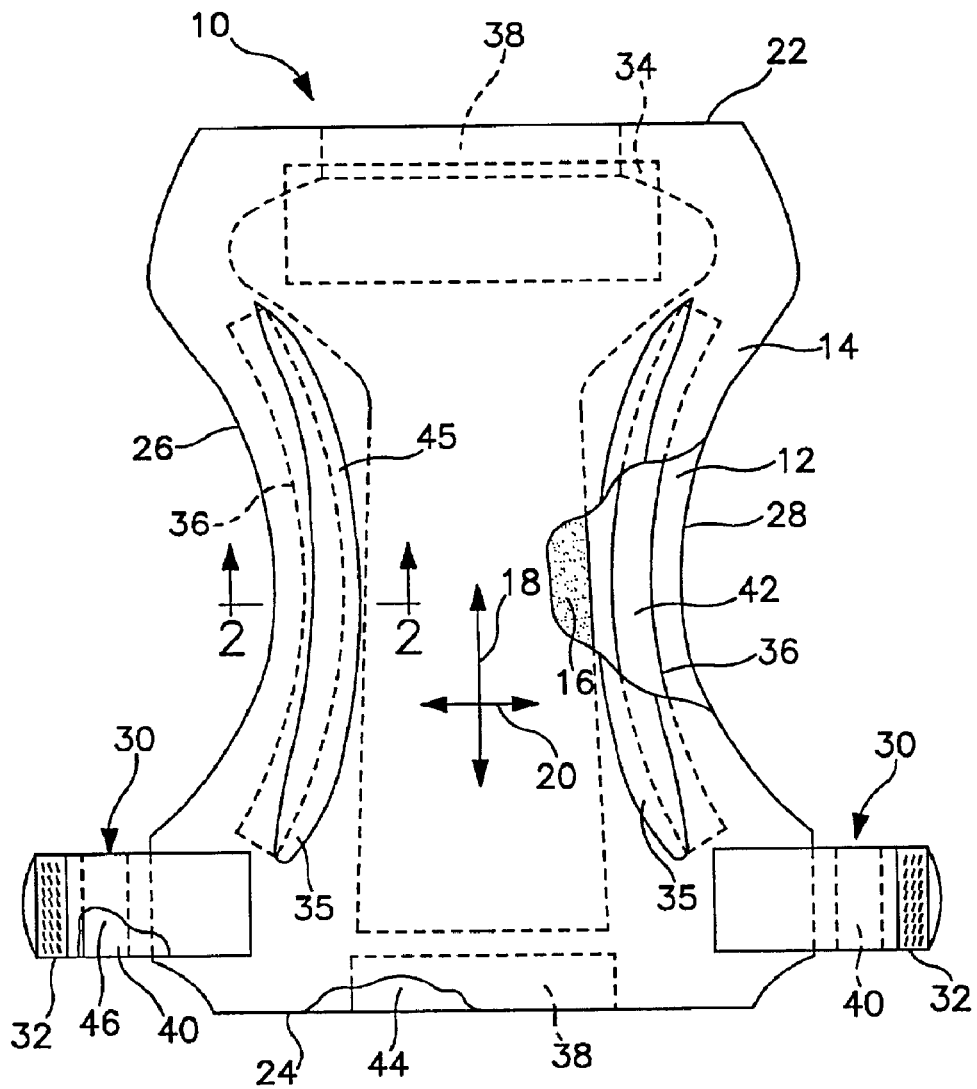
FIG. 1 illustrates a disposable absorbent article according to the present invention.

The disposable absorbent article of the present invention can best be understood by reference to FIG. 1 in which a disposable infant diaper 10 is illustrated. The disposable diaper 10 comprises the following components: a backsheet 12, a topsheet layer 14, and an absorbent structure 16 located between the backsheet layer 12 and the topsheet layer 14.

The diaper 10 has a length in the direction of arrow 18 and a width in the direction of arrow 20. The diaper 10 further comprises a first waist portion 22 and a second waist portion 24. As used herein, the first and second waist portions are those portions of diaper 10 which are generally located at the waist of a wearer when the diaper is in place on the wearer's body. The diaper 10 further defines a first longitudinal marginal portion 26 and a second longitudinal marginal portion 28. The diaper 10 further includes mechanical fastening tabs 30 comprising hook material 32 and a loop material 34 adapted to releasably engage with the hook material 32.

The backsheet layer 12 may comprise a material which is either liquid permeable or liquid impermeable. It is generally preferred that the backsheet layer 12 be formed from a material which is substantially impermeable to liquids. It is also desirable that the backsheet layer 12 be thin and flexible to improve consumer acceptance. For example, a typical backsheet layer can be manufactured from a thin plastic film or other flexible liquid-impermeable material. Examples of the material from which backsheet layer 12 may be formed include a polyethylene film having a thickness of from about 0.012 millimeter (0.5 mil) to about 0.051 millimeter (2.0 mils). If it is desired to present the backsheet layer 12 with a more clothlike feeling, the backsheet layer 12 may comprise a polyethylene film having a nonwoven web laminated to the outer surface thereof such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament (dpf), which nonwoven web has a basis weight of about 24 grams per square meter (0.7 ounce per square yard). Methods of forming such clothlike backsheet layers are known to those skilled in the art.

Further, the backsheet layer 12 may be formed of a nonwoven or woven fibrous web layer which has been constructed or treated to impart a desired level of liquid impermeability to selected regions adjacent to the absorbent structure 16. Still further, the backsheet layer 12 may optionally be composed of a microporous, "breathable" material which permits vapors to escape from the absorbent structure 16 while preventing liquid exudates from passing through the backsheet layer 12.

The topsheet layer 14 of the disposable diaper 10 desirably presents a body-facing surface which is compliant, soft feeling, and nonirritating to the wearer's skin. Further, the topsheet layer 14 may be less hydrophilic than the absorbent structure 16, to present a relatively dry surface to the wearer, and may be sufficiently porous to be liquid permeable, permitting liquid to readily penetrate through its thickness. A suitable topsheet layer 14 may be manufactured from a wide selection of web material such as porous foams, reticulated foams, apertured plastic films, natural fibers (for example, wood or cotton fibers), synthetic fibers (for example, polyester or polypropylene fibers), or a combination of natural or synthetic fibers. The topsheet layer 14 is suitably employed to help isolate the wearer's skin from liquids held in the absorbent structure 16.

Various woven and nonwoven fabrics can be used for the topsheet layer 14. For example, the topsheet layer may be composed of a meltblown or spunbond web of polyolefin fibers. The topsheet layer may also be a bonded-carded web composed of natural and/or synthetic fibers. The topsheet layer may be composed of a substantially hydrophobic material. The hydrophobic material may, optionally, be treated with a surfactant or otherwise processed to impart a desired level of wettability and hydrophilicity. In a particular embodiment of the present invention, the topsheet layer 14 comprises a nonwoven, spunbond, polypropylene fabric composed of about 2.0–5.0 denier per filament fibers formed into a web having a basis weight of about 22 grams per square meter and a density of about 0.06 gram per cubic centimeter. The fabric may be surface treated with about 0.28 weight percent of surfactant commercially available from Rohm and Haas Company under the trade designation Triton X-102.

The absorbent structure 16 of the diaper 10 may suitably comprise a matrix of hydrophilic fibers, such as a web of cellulosic fluff, mixed with particles of a high-absorbency material commonly known as superabsorbent material. In a particular embodiment, the absorbent structure 16 comprises a mixture of superabsorbent hydrogel-forming particles and wood pulp fluff. The wood pulp fluff may be exchanged with a synthetic, polymeric, meltblown fiber or with a combination of meltblown fibers and natural fibers. The superabsorbent particles may be substantially homogeneously mixed with hydrophilic fibers or may be nonuniformly mixed. Alternatively, the absorbent structure 16 may comprise a laminate of fibrous webs and superabsorbent material or other suitable means of maintaining a superabsorbent material in a localized area.

The high-absorbency material can be selected from natural, synthetic and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble, but swellable. Such means can include, for example, physical entanglement, crystalline domains, covalent bonds, ionic complexes, ionic associations, hydrophilic associations such as hydrogen bonding, and hydrophobic associations or Van de Waal forces.

Examples of synthetic, polymeric, high-absorbency materials include the alkaline metal and ammonium salts of poly (acrylic acid) and poly (methacrylic acid), poly (acrylamides), poly (vinyl ethers), maleic anhydride copolymers with vinyl ethers and alpha-olefins, poly (vinyl pyrrolidone), poly (vinyl morpholinone), polylvinyl alcohol), and mixtures and copolymers thereof. Further polymers suitable for use in the absorbent structure include natural and modified natural polymers, such as hydrolyzed acrylonitrile-grafted starch, acrylic acid grafted starch, methylcellulose, carboxymethylcellulose, hydroxypropylcellulose, and the natural gums, such as alginates, xanthan gum, locust bean gum, and the like. Mixtures of natural and wholly or partially synthetic absorbent polymers can also be used in the present invention.

The high-absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent structure in an amount of from about 5 to about 100 weight percent based on total weight of the absorbent structure 16.

Specific examples of disposable diapers suitable for use in the present invention, and other components suitable for use therein, are disclosed in the following U.S. patents and U.S. patent applications: U.S. Pat. No. 4,798,603 issued Jan. 17, 1989, to Meyer et al.; U.S. Pat. No. 5,176,668 issued Jan. 5, 1993, to Bemardin; U.S. Pat. No. 5,176,672 issued Jan. 5, 1993, to Bruemmer et al.; U.S. Pat. No. 5,192,606 issued Mar. 9, 1993, to Proxmire et al.; U.S. Pat. No. 5,415,644 issued May 16, 1995, to Enloe; U.S. Pat. No. 5,509,915, issued Apr. 23, 1996 to Hanson et al., and U.S. Pat. No. 6,245,050, issued Jun. 12, 2001 to Odorzynski et al. Other suitable components include, for example, containment gaskets or flaps 35 and waist flaps.

The disposable absorbent articles of the present invention may include at least one elasticized area formed from an elastomeric, hot melt, pressure-sensitive adhesive film having differential tension, a first component, and a second component, the first and second components being adhered to the elastomeric, hot melt, pressure-sensitive adhesive film. The elastomeric, hot melt, pressure-sensitive adhesive film and the elasticized area formed therewith may have one or more of the following properties:

A. an adhesive bond strength sufficient to adhere the film to said first and second components during use of said disposable absorbent article;

B. an elongation in one area of at least 50 percent;

C. a retractive force in one area of less than 400 grams force per 2.54 cm(1.0 inch) width at 90 percent elongation;

D. a viscosity of less than 70,000 centipoise at 177 degrees C.(350 degrees F.) and E. a cold flow value in one area of less than 20 percent at 54 degrees C.

As used herein, reference to an adhesive bond strength refers to the strength of the bond adhering said first and second components together. The adhesive bond strength can be quantified by the amount of force required to separate the first and second components from one another according to the test method set forth below in connection with the examples. The elastomeric, hot melt, pressure-sensitive differential tension adhesive film of the present invention suitably has an adhesive bond strength, as determined by the test method set forth below in connection with the examples, of at least 100 grams force per inch (2.54 cm) width, suitably of at least 200 grams force per inch (2.54 cm) width, alternatively of at least 400 grams force per inch (2.54 cm) width, alternatively of at least from about 200 grams force per inch (2.54 cm) width to about 700 grams force per inch width.

As used herein, reference to the elongation of the elasticized area formed with the elastomeric, hot melt, pressure-sensitive differential tension adhesive film refers to the elongation of the elasticized area and is suitably determined as set forth below in connection with the examples. The elasticized area formed with the elastomeric, hot melt, pressure-sensitive differential tension adhesive film suitably has at least a portion with an elongation of at least 50 percent, alternatively of at least 150 percent, alternatively of from about 50 percent to about 250 percent.

As used herein, reference to the retractive force of the elasticized area formed with the elastomeric, hot melt, pressure-sensitive differential tension adhesive film refers to the retractive force exhibited by at least one portion of the elasticized area one minute after stretching to 90% of the elongation of the elasticized area, and is suitably determined as set forth below in connection with the examples. At least a portion of the elasticized area suitably has a retractive force of less than about 400 grams force per inch (2.54 cm) width, alternatively of less than about 275 grams force per inch (2.54 cm) width, alternatively of from about 100 grams force per inch (2.54 cm) width to about 250 grams force per inch (2.54 cm) width.

As used herein, reference to the viscosity of the elastomeric, hot melt, pressure-sensitive differential tension adhesive film refers to the viscosity, in centipoise at 176 degrees C. (350 degrees F.) as determined by a Brookfield Model DV-111 Programmable Rheometer (spindle size of 27) commercially available from E. Johnson Engineering & Sales Co., Elmhurst, Ill. 60126. A suitable test method is set forth in American Society for Testing and Materials (ASTM) test method D-3236. The elastomeric, hot melt, pressure-sensitive differential tension adhesive films of the present invention suitably have a viscosity of less than 70,000 centipoise at 176 degrees C. (350 degrees F.), alternatively of less than 50,000, alternatively of from about 20,000 to about 35,000. This low viscosity enables the use of hot melt extrusion equipment which can be easier to use than typical thermoplastic material screw driven extrusion equipment.

Reference to the cold flow value of the elasticized area formed with the elastomeric, hot melt, pressure-sensitive adhesive film refers to the amount of elastic composite growth after the elasticized area has been exposed to a temperature of 54 degrees C. for a period of 24 hours. The cold flow values of the elasticized areas are suitably determined as set forth below in connection with the examples. At least a portion of the elasticized area formed with the elastomeric, hot melt, pressure-sensitive differential tension adhesive films of the present invention suitably have a cold flow value of less than about 20 percent, alternatively of less than 15 percent, alternatively of from about 5 percent to about 10 percent.

A number of elastomeric components are known for use in the design and manufacture of disposable absorbent articles. For example, disposable absorbent articles are known to contain elasticized leg cuffs, elasticized waist portions, elasticized containment gaskets, and elasticized fastening tabs. Thus, with reference to FIG. 1, the elasticized areas of the disposable absorbent articles according to the present invention may form elasticized leg cuffs 36, waist elastics 38, elasticized fastening tabs 40, and elasticized containment gaskets 35. That is, the elastomeric, hot melt, pressure-sensitive differential tension adhesive films of the present invention may be used in, or as, components of the disposable diapers to form, without limitation, the elasticized areas 42, 44, 45 and 46 indicated as defining elasticized leg cuff 36, waist elastics 38, containment gaskets 35 and elasticized fastening tabs 40, respectively.

The disposable absorbent articles of the present invention need only have one elasticized area formed from an elastomeric, hot melt, pressure-sensitive differential tension adhesive film. The elasticized areas are suitably formed by incorporating the hot melt, pressure-sensitive adhesive film to one or more components of the disposable absorbent article. For example, the elasticized hot melt, pressure-sensitive differential tension adhesive films may be applied to a first component such as the backsheet 12, the topsheet 14, the absorbent structure 16 or a carrier sheet, or the like, which first component may then be brought into contact with and adhered to a second component of the diaper by applying pressure to the film. The second component may be a separate component or may be a different portion of the first component. For example, the elastomeric, hot melt, pressure-sensitive differential tension adhesive film may be applied to the backsheet 12 which is then adhered to the topsheet 14 to form an elasticized area which functions as a leg 36 or waist 38 elastic, or the topsheet 14 may be folded in various manners to create integral leg cuffs with the film contained therein. Alternatively, the elastomeric, hot melt, pressure-sensitive adhesive film may be applied to a thin carrier or facing sheet which is applied to the backsheet 14 or topsheet 12 to form a separate elasticized component such as a barrier flap, or containment gasket 35, not integrally created with the backsheet or topsheet. It is also contemplated that the film may be used by itself as a functional component of the diaper without additional facing material.

If the elastomeric, hot melt, pressure-sensitive differential tension adhesive film is applied directly, or via a carrier sheet, to one or more components of a disposable absorbent article without first being stretched, the component(s) to which it is applied may need to be capable of being stretched in a least one direction in order to produce an elasticized area. For example, the component could be necked, or gathered, in order to allow it to be stretched after application of the elastomeric, hot melt, pressure-sensitive differential tension adhesive film. Various post treatments, such as treatment with grooved rolls, which alter the mechanical properties of the garment component, are also suitable for use.

After being applied to the disposable absorbent article, the elastomeric, hot melt, pressure-sensitive differential tension adhesive film typically contracts to gather the components of the disposable absorbent article to which it is attached. The elastomeric, hot melt, pressure-sensitive differential tension adhesive films are capable not only of introducing differential degrees of elasticity to the disposable absorbent article, but are also capable of providing a construction adhesive function. That is, the pressure-sensitive adhesive films can adhere together the components of the disposable absorbent article to which they are in contact. Thus, in one embodiment, it is preferred that the elasticized area formed from the elastomeric, hot melt, pressure-sensitive differential tension adhesive film described above be free of other adhesive materials, preferably of both other adhesive materials and other elastomeric materials. It is also possible that the elastomeric, hot melt, pressure-sensitive differential tension adhesive films do not constrict upon cooling but, instead, tend to retract to approximately their original dimension after being elongated during use of the product. This may necessitate that the component of the disposable absorbent article to which the elastomeric, hot melt, pressure-sensitive differential tension adhesive film is attached be capable of being elongated in at least one direction.

Figure 3:
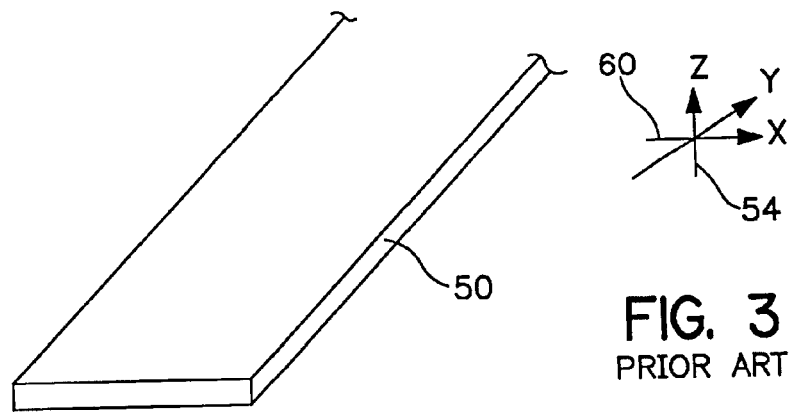
FIG. 3 illustrates an EBA film as known in the art.

As known in the art, a flat film 50 as seen in FIG. 3 has been contemplated for use as an EBA (elastic barrier adhesive) film layer. By applying the elastomeric, hot melt, pressure-sensitive differential tension adhesives to the disposable absorbent article in the form of a film, the elasticized area 42 (e.g., in FIG. 1) may be created. The film of the known art was taught to have a thickness of about 0.001 inch to about 0.05 inch, alternatively of from about 0.001 to about 0.01 (about 0.00254 cm to about 0.0254 cm), and a width of from about 0.05 inch, to about 3.0 inches (about 0.127 cm to about 7.62 cm), alternatively of from about 0.5 inch to about 1.5 inches (about 1.27 cm to about 3.81 cm). The film of the known art can impart barrier properties to the elasticized area formed therewith, however it will not impart differential elasticity to the area as in the present invention.

Suitable elastomeric, hot melt, pressure-sensitive adhesives for the making of the films of the present invention comprise elastomeric polymers, tackifying resins, plasticizers, oils and antioxidants. Such elastomeric, hot melt, pressure-sensitive adhesives are available from Bostik-Findley, Inc., Wauwatosa, Wis. under the trade designations H2503 and H2504 or others cited herein.

Figure 2:
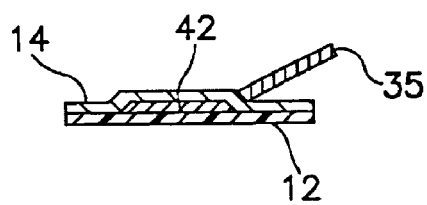
FIG. 2 is a cross-sectional view taken along line 2—2 of FIG. 1.

FIG. 2 illustrates a cross-sectional view taken along line 2—2 of FIG. 1.

Test Methods
Adhesive Bond Strength

The adhesive bond strength of an elasticized area according to the present invention is determined as follows. A test sample of the elasticized area is cut from the absorbent product. The elasticized area preferably has the dimensions of 2.0 inches wide by 4.0 inches long (5.08 cm by 10.16 cm). If the elasticized area is not this large, the largest sample possible (but less than 2.0 inches by 4 inches) is used for testing. It is not necessary for the sample to be tested to have an elastomeric, hot melt, pressure-sensitive differential tension adhesive film located continuously across the length and/or width of the sample. Thus, for example, if the elastomeric, hot melt, pressure-sensitive differential tension adhesive film is applied between first and second components in an intermittent application, a test sample having the stated length and width can be cut from the product so as to encompass that area of the elasticized area having generally the greatest coverage of the elastomeric, hot melt, pressure-sensitive differential tension adhesive film across its width and length. The adhesive film bond strength is determined through the use of a tensile tester such as a SINTECH tensile tester commercially available from the Sintech Co., Carry, N.C., Model No. II. A 90 degree peel adhesion test is run in order to determine the grams of force needed to pull apart the first and second components of the elasticized area. Such a test method is generally described in Pressure Sensitive Tape Counsel Test Method 1. Specifically, 1.25 inches (3.175 cm) or more of the 4 inch length of the test sample has the first and second components peeled apart. The first component is then clamped in the upper jaw of the tensile tester, and the second component is clamped in the lower jaw of the tensile tester. The tensile tester is set to the following conditions:
Crosshead Speed: 300 millimeters per minute
Full-scale load: 5,000 grams
Start measurements: 10 millimeters
Gauge Length: (Jaw spacings) 1.0 inch (2.54 cm)

The Sintech tensile tester is then engaged. The test is terminated after approximately 100 millimeters on a 2 inch by 4 inch sample. Twenty data points per second are collected for a total of about 400 data points. The average of these data points is reported as the adhesive film bond strength. The results from the tensile tester are normalized to a sample having a width of 1 inch. At least three test samples are subjected to the above testing with the results being averaged and normalized to produce the reported adhesive film bond strength.

Elongation

The elongation of an elasticized area according to the present invention is suitably determined as follows. A 1 inch wide by 4 inch long elasticized area is provided. The central 3 inch (7.62 cm) area of the sample is marked. The test sample is then stretched to its maximum length, and the distance between the marks is measured and recorded as the "stretched to stop length." The percent elongation is determined according to the following formula:

$$\frac{\text{stretched to stop length (in inches)} - 3}{3} \times 100$$

If a 1 inch by 4 inch elasticized area is not available, the largest sample possible (but less than 1 inch by 4 inch) is used for testing with the test method being adjusted accordingly.

Retractive Force

The retractive force of an elasticized area according to the present invention is determined on a test sample having a width of 1 inch and a length of 3 inches. A test apparatus having a fixed clamp and an adjustable clamp is provided. The adjustable clamp is equipped with a strain gauge commercially available from S.A. Mieier Co. under the trade designation Chatillon DFIS2 digital force gauge. The test apparatus can elongate the test sample to a given length. One longitudinal end of the test sample is clamped in the fixed clamp of the test apparatus with the opposite longitudinal end being clamped in the adjustable clamp fitted with the strain gauge. The test sample is elongated to 90 percent of its elongation (as determined by the test method set forth above). The retractive force is read from the digital force gauge after 1 minute. At least three samples of the elasticized area are tested in this manner with the results being averaged and reported as grams force per inch width.

Cold Flow

The cold flow properties of the elasticized area according to the present invention are determined on a test sample having a width of 1 inch and a length of 3 inches. The test sample is placed in an aging room at a temperature of 54 degrees C. for 24 hours. At the end of that time, the test sample is removed from the aging room and the length of the test sample is measured and recorded as the "aged length." The percent cold flow is determined by the following formula: [(Aged length minus original length)/original length]times 100.

Examples of known laminates using EBA films are set forth in Examples 1–3 below.

EXAMPLE 1

An elastomeric, hot melt, pressure-sensitive adhesive available from Bostik-Findley, Inc. under the trade designation of H-2504 was processed through a Nordson hot melt glue system (available from the Nordson Corporation) at a temperature of 350 degrees F. The material was passed through a slot die having a width of 6 inches and a uniform thickness of 8 mils. The elastomeric, hot melt, pressure-sensitive adhesive film was then formed on a chill roll having a temperature of 56–57 degrees F. traveling at a speed of 6 feet per minute. The elastomeric, hot melt, pressure-sensitive adhesive film was then stretched to approximately 575–600% of its length and was brought into contact with two webs of material. The first web of material was a 0.5 ounce per square yard, 2 denier per filament polypropylene spunbond material, thermally bonded to a 0.4 mil (0.3 ounce per square yard) cast film. The second web of material was a pointbonded carded web of 2–2.5 denier per filament side by side polyethylene/polypropylene bicomponent fibers having a basis weight of 0.7 ounce per square yard. Both web materials had a width greater than the quenched elastomeric, hot melt, pressure-sensitive adhesive film. The quenched elastomeric, hot melt, pressure-sensitive adhesive film was placed between the two web materials and run through a compression roll having a nip pressure of 100 pounds per square inch. The elastomeric, hot melt pressure-sensitive adhesive film was bonded to the film side of the first web. The finished laminate was allowed to retract and was collected. The finished laminate had the following properties; an adhesive bond strength of 655.2 grams per one inch width; an elongation of 150 percent; a 125 gram retractive force and a cold-flow value of 0 percent.

EXAMPLE 2

An elastomeric, hot melt, pressure-sensitive adhesive available from Bostik-Findley, Inc. under the trade designation H-2504 was processed through a Nordson hot melt glue system at a temperature of 350 degrees F. The material was passed through a slot die having a width of 6 inches and a uniform thickness of 8 mils. The elastomeric, hot melt, pressure-sensitive adhesive film was then placed on a chill roll having a temperature of 56–57 degrees F. traveling at a speed of 6 feet per minute. The elastomeric, hot melt, pressure-sensitive adhesive film was then stretched approximately 575–600 percent of its length and was brought into contact with two pointbonded, bonded carded webs of 2–2.5 denier per filament side-by-side polyethylene/polypropylene bicomponent fiber webs having a basis weight of 0.7 ounce per square yard. The quenched elastomeric, hot melt, pressure-sensitive adhesive was located between the two web materials and run through a compression roll having a nip pressure of 100 pounds per square inch. The finished laminate was allowed to retract and was collected. The finished laminate had the following properties; an adhesive bond strength of 457.8 grams per one inch width; an elongation of 160 percent; a 133 gram retractive force; and a cold-flow value of 8.3 percent.

EXAMPLE 3

An elastomeric, hot melt, pressure-sensitive adhesive available from Bostik-Findley, Inc., under the trade designation of H-2503 was processed through a Nordson hot melt glue system at a temperature of 375 degrees F. The material was passed through a slot die having a width of 6 inches and a uniform thickness of approximately 3 mils. The elastomeric, hot melt, pressure-sensitive adhesive was then placed on a chill roll having a temperature of 56–57 degrees F. traveling at a speed of approximately 20 feet per minute. The elastomeric, hot melt, pressure-sensitive adhesive was then stretched 575 percent of into contact with two webs of polypropylene spunbond material having a basis weight of 0.7 ounce per square yard and being formed from 3 denier per filament fibers. Both spunbond materials have a width greater than the quenched elastomeric, hot melt, pressure-sensitive adhesive. The quenched elastomeric, hot melt, pressure-sensitive adhesive was placed between the two spunbond layers and passed through a compression nip roll having a nip pressure of 100 pounds per square inch. The finished laminate was allowed to retract and was collected. The finished laminate had the following properties; an adhesive bond strength of 612 grams per one inch width; an elongation of 105 percent; a 116 gram retractive force; and a cold-flow value of 8.3 percent.

The films made according to the above Examples 1–3 can be suitably modified during hot melt processing, typically through use of different die structures as evidenced by the film structures of FIGS. 4–8 described below, to produce at least two different dimensions in the Z axis of the film to produce the advantages of the present invention.

EXAMPLE 4

A first, flat-profiled film such as seen in FIG. 3, and a second, differential profiled film such as seen in FIG. 14, were produced from elastomeric, hot melt, pressure-sensitive adhesive, available from Bostik-Findley, Inc., of Wauwatosa, Wis. under the trade designation HX-2695-01, as processed through a Nordson hot melt glue system at a temperature of 380 degrees F. The base layer was passed through a slot die having a width of 6 inches and a uniform thickness of 10 mils. For the second film, a second 10 mil layer, about three-eighths inch wide was added to the base layer to create the differential profile. The elastomeric, hot melt, pressure-sensitive adhesive films were then placed on a chill roll having a temperature of 56–57 degrees F. traveling at a speed of 10 feet per minute. The elastomeric, hot melt, pressure-sensitive adhesive films were then stretched approximately 500 percent of their length and brought into contact with two polypropylene spunbond nonwoven webs having a basis weight of 0.5 ounce per square yard. The quenched elastomeric, hot melt, pressure-sensitive adhesive films were located between the two web materials and run through a compression roll having a nip pressure of 60 pounds per square inch. The finished laminates were stretched and cut into two inch wide sample strips. The first laminate had an elongation of 290 percent; and a 162 gram retractive force. The second laminate had an elongation of 346 percent; and a 240 gram retractive force. Adhesive bond strengths and cold-flow values were not measured but are believed to be comparable to the other examples.

Figure 4:
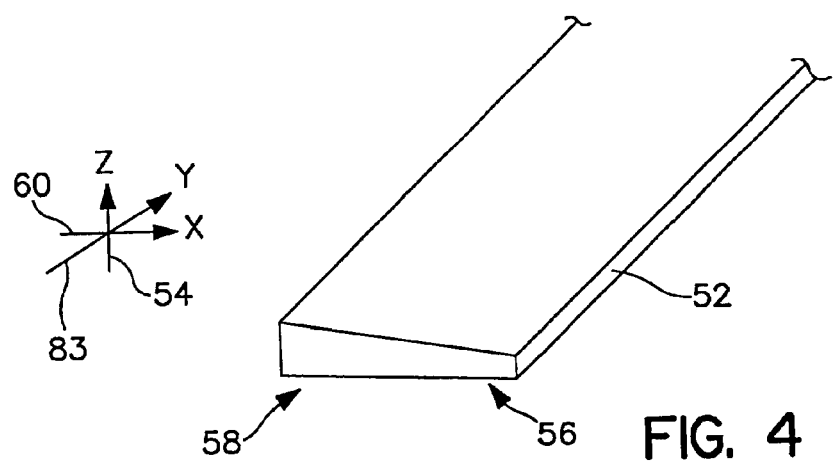
FIG. 4 illustrates one shape of an EBA film with regular sides according to the present invention which provides differential elasticity through a variable Z axis dimension.

Referencing FIG. 4, there is illustrated an EBA film 52 having a variable Z axis dimension, with the X, Y and Z axis directions being indicated by arrows 60, 83 and 54 respectively, according to the present invention. FIG. 4 illustrates one shape of an EBA film with regular sides which provides differential elasticity and tension through a variable Z axis dimension. The thin side 56 of the film 52 will provide less tension than the thick side 58 of the film thus resulting in a differential elasticity over the width of the film in the X-axis direction 60.

Figure 5:
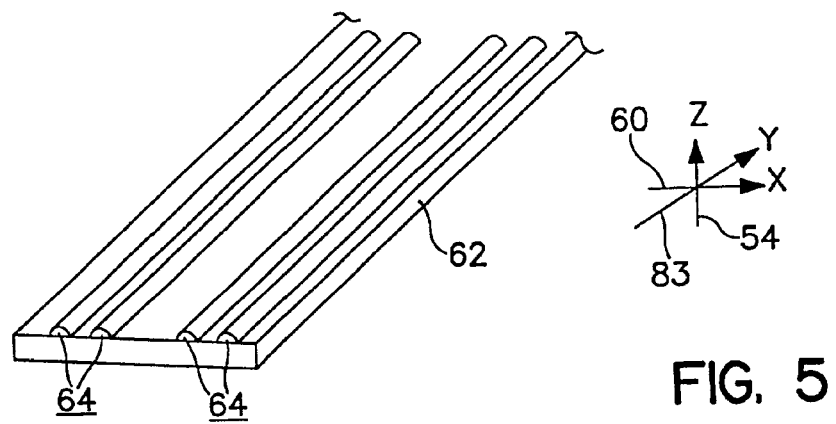
FIG. 5 illustrates another shape of an EBA film with a cross section of rounded crenellations at irregular spacing according to the present invention which provides differential elasticity through a variable Z axis dimension.

FIG. 5 illustrates another shape of an EBA film 62 with a cross section through the X axis direction 60 showing rounded crenellations, collectively 64, placed in two groups of two crenellations separated by a distance in the X axis direction 60, with each group having a different spacing between its crenellations to provide differential elasticity through a variable Z axis dimension. Various shapes and spacings of crenellations may be utilized to achieve the purposes of the present invention.

Figure 6:
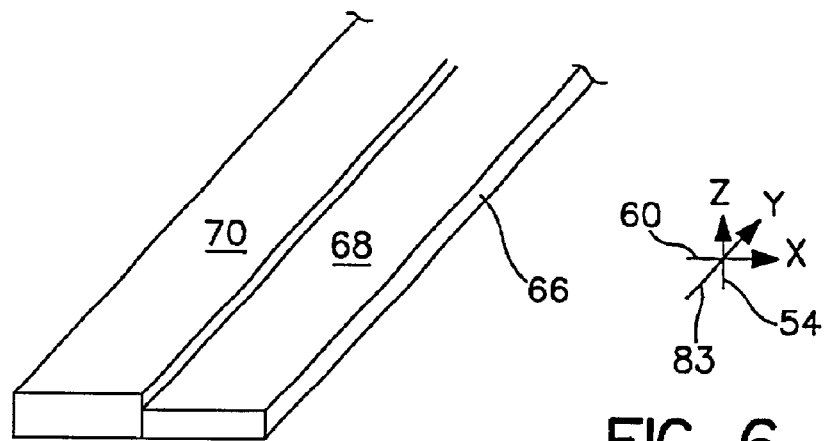
FIG. 6 illustrates another shape of an EBA film with a staggered cross section revealing bilateral sides of the film which have been co-extruded of different material compositions according to the present invention to provide differential elasticity through a variable Z axis dimension.

FIG. 6 illustrates another shape of an EBA film 66 with a cross section through the X axis direction 60 showing staggered bilateral halves of the film 68, 70 of different height which have been co-extruded of different material compositions such as Bostik-Findley, Inc. formulations H2503 and H2504 to provide differential elasticity through a variable Z axis dimension and through the different elasticity inherent in the two different formulations. The demarcation line between the bilateral halves may be somewhat exaggerated from actual coextrusion hot melt processing to clearly illustrate the halves.

Figure 7:
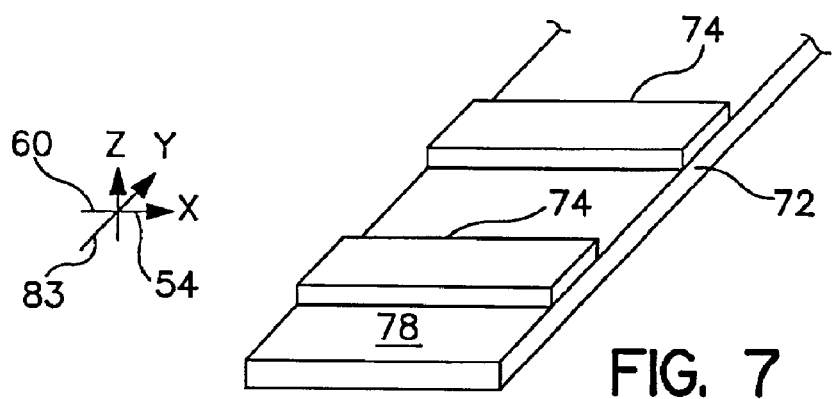
FIG. 7 illustrates another shape of an EBA film with a variable Z axis dimension through alternatively depositing more material in the film at even intervals along the direction of manufacture.

FIG. 7 illustrates another shape of an EBA film 72 with a cross section through the Y axis direction 83 showing a variable Z axis dimension created through alternatively depositing more material to form mounds, collectively 74, in the film 72 at even intervals along the direction of manufacture in the Y-axis direction 83 by varying the pressure of the hot melt feed pump. Various shapes and spacings of mounds 74 may be utilized to achieve the purposes of the present invention. The demarcation line between the mounds 74 and the more planar aspect 78 of the film may be somewhat exaggerated from actual hot melt extrusion processing to clearly illustrate the mounds 74.

Figure 8:
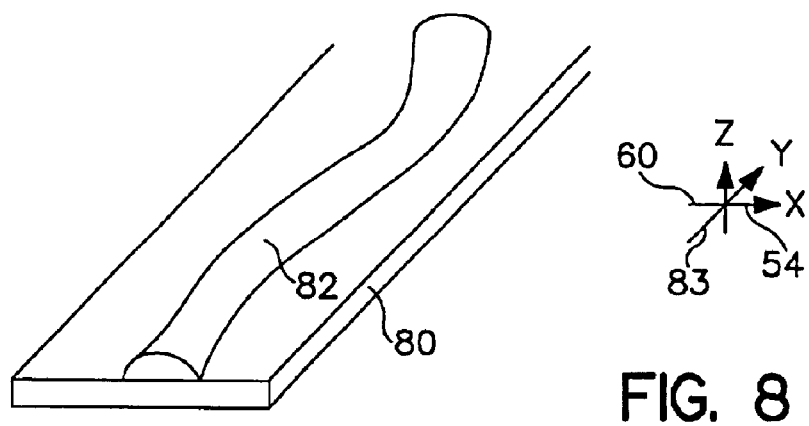
FIG. 8 illustrates another shape of an EBA film with a variable Z axis dimension through deposition of more material in a serpentine mound along the direction of manufacture.

FIG. 8 illustrates another shape of an EBA film 80 with a cross section through the X axis direction 60 showing a variable Z axis dimension created through deposition of more material in a mound 82 displaced in a serpentine curve through the X-Y place of the film 80 and extending in the Y axis direction 83, i.e., along the direction of manufacture through use of a moving gate on the hot melt die structure. Through this configuration, differential tension may also be exerted along more than one axis of the film 80.

Figure 9:
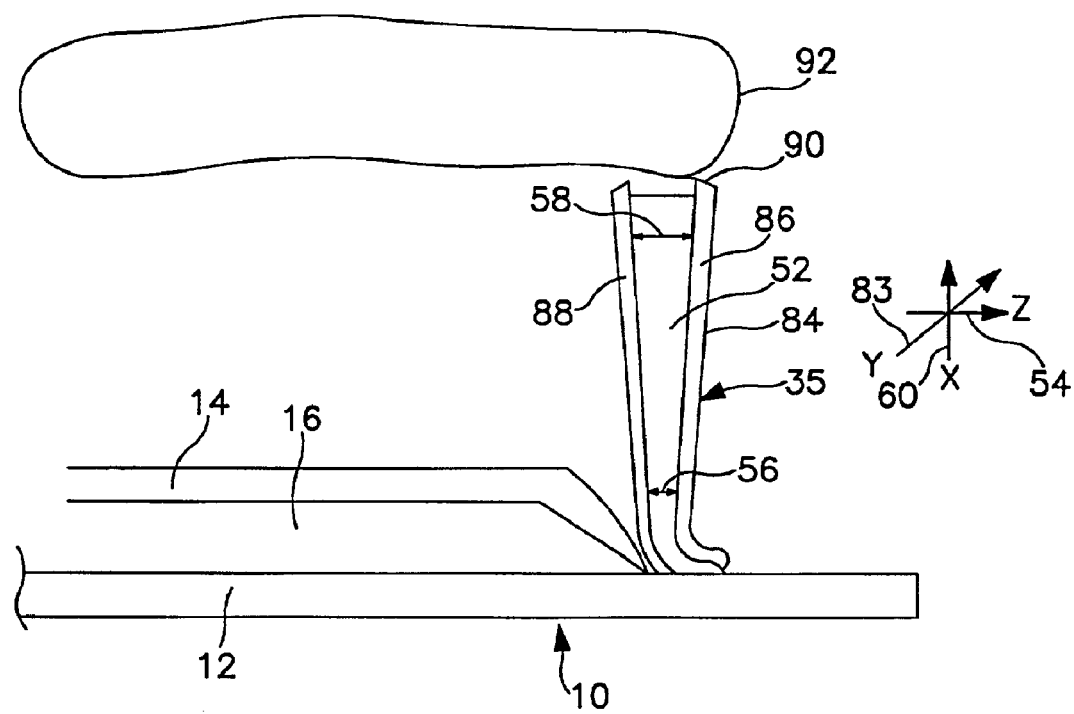
FIG. 9 illustrates a containment gasket of the diaper of FIG. 1 utilizing a laminate according to the present invention with an area of high tension on the outer edge of the containment gasket.

FIG. 9 schematically illustrates one leg containment gasket 35 of the diaper 10 of FIG. 1 utilizing a laminate 84 according to the present invention. Outer facing material 86 and inner facing material 88 are adhered to the pressure sensitive differential tension adhesive film 52 of FIG. 5 having a first thin dimension 56 of low tension near the absorbent structure 16 of the diaper 10 and a second thicker dimension 58 of high tension towards the outer, or free edge 90 of the gasket 35. The facing materials 86, 88 may be any material or materials suitable to the function of the gasket 35 such as spun bond nonwovens which will not irritate the body of the wearer 92. As known in the art, a diaper 10, upon becoming loaded with a fluid, will sag under the force of gravity away from the body of the wearer 92. Through provision of a differential elastic with an area of higher tension on the free end of the gasket 35, the gasket 35 is made to extend transversely to the main body of the diaper 10 thereby providing gasketing and preventing leakage to the exterior of the diaper. The garment designer of ordinary skill will appreciate that the areas of high tension elastic may be selectively placed according to the dictates of fit and appearance for the particular elasticized area or component of a particular style of garment.

Referencing FIGS. 10–13, and FIG. 1, a differential tension area of the diaper 10 (FIG. 1), such as an area of leg elastic 36 (FIG. 1), is illustrated in isolation from the diaper 10, with FIG. 10 being a top view corresponding to a portion of the left hand side of the view of FIG. 1, and FIGS. 11–13 being cross-sectional views taken along lines 11—11, 12—12 and 13—13 of FIG. 10, respectively. Referencing particularly FIGS. 10 and 13, the pressure sensitive differential tension elastomer adhesive film 94 has nonwoven facings, illustrated for example by topsheet 14 and backsheet 12. The thin dimension 56 of the elastomer 94 can be placed so as to be proximal absorbent section 16 of the diaper 10 (FIG. 1) while the thicker dimension 58 of the elastomer 94 would be placed near the first longitudinal marginal portion 26 of the diaper 10 (FIG. 1). Referencing FIGS. 10 and 11, the area of higher tension, i.e. the thicker dimension 58 of the elastomer 94, has exerted a higher tensioning force in returning to the relaxed state on both the nonwoven topsheet 14 and the nonwoven backsheet 12 resulting in higher and more closely spaced rugosities, collectively 96, being formed in the nonwovens as seen in the cross sectional view of FIG. 11 taken along line 11—11 of FIG. 10. Referencing FIGS. 10 and 12, the area of lower tension, i.e. the thinner dimension 56 of the elastomer 94, has exerted a lower tensioning force in returning to the relaxed state on both the nonwoven topsheet 14 and the nonwoven backsheet 12 resulting in lower and more widely spaced rugosities, collectively 98, being formed in the nonwovens as seen in the cross sectional view of FIG. 12 taken along line 12—12 of FIG. 10.

While the present invention has been described in terms of the specific embodiments set forth herein, those skilled in the art will recognize numerous variations and alterations thereof which are intended to be within the scope of the claims appended hereto.

We claim:

1. An elastomeric, hot melt, pressure-sensitive adhesive film having major surfaces in the X-Y plane and having at least two different material thicknesses in the Z axis, the different material thicknesses resulting in differential tensions when the elastomeric film is stretched; and
wherein the elastomeric film has a cross section through the Z axis with a crenellated profile.

2. The elastomeric, hot melt, pressure-sensitive adhesive film according to claim 1 wherein the elastomeric film comprises a first material composition and a second material composition.

3. The elastomeric, hot melt, pressure-sensitive adhesive film according to claim 2 wherein the elastomeric film is formed by hot melt coextrusion of the first material composition and the second material composition.

4. The elastomeric, hot melt, pressure-sensitive adhesive film according to claim 1 further comprising:
   a first facing layer component adhered to a first surface of the elastomeric adhesive film to form a laminate,
   the laminate being capable of elongation in a first direction, the laminate having a non-elongated original length in the first direction, the laminate being retractable after elongation to a length substantially equivalent to the original length.

5. The elastomeric, hot melt, pressure-sensitive adhesive according to claim 4 further comprising:
   a second facing layer component adhered to a second surface of the elastomeric adhesive film to form a laminate.

6. An absorbent article incorporating the laminate of claim 4.

7. The elastomeric, hot melt, pressure-sensitive adhesive film according to claim 1 wherein the elastomeric adhesive film forms a liquid barrier.

8. An absorbent article incorporating the elastomeric film of claim 1.

9. An elastomeric, hot melt, pressure-sensitive adhesive film having major surfaces in the X-Y plane and having at least two different material thicknesses in the Z axis, the different material thicknesses resulting in differential tensions when the elastomeric film is stretched; and
wherein the elastomeric film has a raised area curving serpentine through the X-Y plane of the film.

10. The elastomeric, hot melt, pressure-sensitive adhesive film according to claim 9 wherein the elastomeric film comprises a first material composition and a second material composition.

11. The elastomeric, hot melt, pressure-sensitive adhesive film according to claim 10 wherein the elastomeric film is formed by hot melt coextrusion of the first material composition and the second material composition.

12. The elastomeric, hot melt, pressure-sensitive adhesive film according to claim 9 further comprising:
   a first facing layer component adhered to a first surface of the elastomeric adhesive film to form a laminate,
   the laminate being capable of elongation in a first direction, the laminate having a non-elongated original length in the first direction, the laminate being retractable after elongation to a length substantially equivalent to the original length.

13. The elastomeric, hot melt, pressure-sensitive adhesive according to claim 12 further comprising:
   a second facing layer component adhered to a second surface of the elastomeric adhesive film to form a laminate.

14. The elastomeric, hot melt, pressure-sensitive adhesive film according to claim 9 wherein the elastomeric adhesive film forms a liquid barrier.

15. An absorbent article incorporating the laminate of claim 12.

16. An absorbent article incorporating the elastomeric film of claim 9.

17. An elastomeric, hot melt, pressure-sensitive adhesive film having major surfaces in the X-Y plane and having at least two different material thicknesses in the Z axis, the different material thicknesses resulting in differential tensions when the elastomeric film is stretched; and
wherein the elastomeric film has a cross section through the Z axis with a regular profile formed of unbroken lines.

18. The elastomeric, hot melt, pressure-sensitive adhesive film according to claim 17 wherein the elastomeric film comprises a first material composition and a second material composition.

19. The elastomeric, hot melt, pressure-sensitive adhesive film according to claim 18 wherein the elastomeric film is formed by hot melt coextrusion of the first material composition and the second material composition.

20. The elastomeric, hot melt, pressure-sensitive adhesive film according to claim 17 further comprising:
   a first facing layer component adhered to a first surface of the elastomeric adhesive film to form a laminate,
   the laminate being capable of elongation in a first direction, the laminate having a non-elongated original length in the first direction, the laminate being retractable after elongation to a length substantially equivalent to the original length.

21. An absorbent article incorporating the laminate of claim 20.

22. The elastomeric, hot melt, pressure-sensitive adhesive according to claim 20 further comprising:
   a second facing layer component adhered to a second surface of the elastomeric adhesive film to form a laminate.

23. The elastomeric, hot melt, pressure-sensitive adhesive film according to claim 17 wherein the elastomeric adhesive film forms a liquid barrier.

24. An absorbent article incorporating the elastomeric film of claim 17.

25. A disposable absorbent article having a length and a width defining first and second waist portions and first and second longitudinal marginal portions, the article comprising:
   a backsheet layer;
   a topsheet layer;
   an absorbent structure located between said topsheet layer and the backsheet layer; and
   at least one elasticized area comprising an elastomeric adhesive film comprising a hot melt pressure sensitive adhesive elastomeric film having at least two different dimensions in the Z axis including at least one of a cross section through the Z axis with a crenellated profile, a raised area curving serpentine through the X-Y plane of the film, and a cross section through the Z axis with a regular profile formed of unbroken lines, the elasticized area being capable of elongation in a first direction, the elasticized area having a non-elongated original length in the first direction, the elasticized area being retractable after elongation to a length substantially equivalent to the original length and said elasticized area having a cold flow value of less than 20 percent at 54 degrees C.

26. The disposable absorbent article of claim 25 wherein the elasticized area is disposed adjacent a leg opening in said article.

27. The disposable absorbent article according to claim 25 wherein the elasticized area is present in a containment gasket.

28. The disposable absorbent article of claim 25 wherein the elasticized area is disposed in one of the first and second waist portions.

29. The disposable absorbent article of claim 25 wherein adhesives present in the elasticized area consist of said elastomeric adhesive film and wherein elastic elements present m the elasticized area consist of said elastomeric adhesive film.

30. The disposable absorbent article of claim 25 wherein the elastomeric adhesive forms a liquid barrier.

31. A disposable absorbent article having a length and a width defining first and second waist portions and first and second longitudinal marginal portions, the article comprising the following components:

a backsheet layer;

a topsheet layer, and an absorbent structure located between said topsheet layer and the backsheet layer, the article including at least one elasticized area fanned from an elastomeric, hot melt, pressure-sensitive adhesive film having at least two different Z axis dimensions including at least one of a cross section through the Z axis with a crenellated profile, a raised area curving serpentine through the X-Y plane of the film, and a cross section through the Z axis with a regular profile formed of unbroken line, the elasticized area having a first component and a second component adhered to the elastomeric hot melt pressure-sensitive adhesive film, the elasticized area being elongateable in a first direction, the elasticized area having an original length in the first direction, the elasticized area being retractable after elongation to a length substantially equivalent to the original length, the elasticized area having the following properties:

a) an adhesive bond strength sufficient to adhere the first and second components together during use of said disposable absorbent article;

b) an elongation in at least one portion of the elasticized area of at least 50 percent;

c) a retractive force in at least a first portion of the elasticized area of less than 400 grams force per inch width at 90 percent elongation and a retractive force in a second portion of the elasticized area greater than the refractive force in the first portion;

d) a viscosity in at least one portion of the elasticized area of less than 70,000 centipoise at 177 degrees C.; and e) a cold flow value in at least one portion of the elasticized area of less than 20 percent at 54 degrees C.

32. The disposable absorbent article according to claim 31 wherein the elastomeric, hot melt, pressure-sensitive adhesive has an adhesive bond strength of at least 100 grams force per inch width.

33. The disposable absorbent article according to claim 31 wherein said elasticized area has an elongation of from 50 percent to 200 percent.

34. The disposable absorbent article according to claim 31 wherein the elasticized area has a retractive force of from about 100 grams force per inch width to about 250 grams force per inch width in the first portion.

35. The disposable absorbent article according to claim 31 wherein the elasticized area has a cold flow value of less than 15 percent at 54 degrees C.

36. The disposable absorbent article according to claim 31 wherein the elasticized area is present in said first and second longitudinal marginal portions.

37. The disposable absorbent article according to claim 31 wherein the elasticized area is present in at least one of said first and second waist portions.

38. The disposable absorbent article according to claim 31 wherein the elasticized area is present in a containment gasket.

39. The disposable absorbent article of claim 31 wherein the elastomeric adhesive forms a liquid barrier.

* * * * *